(12) United States Patent
Blank et al.

(10) Patent No.: US 6,610,530 B2
(45) Date of Patent: Aug. 26, 2003

(54) METHOD OF IMPROVING BIOMASS YIELD OF LACTIC ACID BACTERIAL CULTURES

(75) Inventors: Lars Blank, Kamen (DE); Peter Ruhdal Jensen, Gentofte (DK); Jensen B. Koebmann, Stensted (DK)

(73) Assignee: Danmarks Tekniske Universitet, Lyngby (DK)

( * ) Notice: Subject to any disclaimer, the term of this patent is extended or adjusted under 35 U.S.C. 154(b) by 0 days.

(21) Appl. No.: 09/898,490

(22) Filed: Jul. 5, 2001

(65) Prior Publication Data

US 2002/0034815 A1 Mar. 21, 2002

Related U.S. Application Data

(60) Provisional application No. 60/216,356, filed on Jul. 5, 2000.

(51) Int. Cl.$^7$ ................................. L12N 1/20

(52) U.S. Cl. .............................. 435/252.9; 435/252.1; 435/253.6; 435/244

(58) Field of Search ........................ 435/252.1, 252.9, 435/253.6, 244

(56) References Cited

U.S. PATENT DOCUMENTS

| | | | | |
|---|---|---|---|---|
| 3,655,396 | A | * | 4/1972 | Goto et al. |
| 4,115,199 | A | * | 9/1978 | Porubcan et al. |
| 5,075,226 | A | * | 12/1991 | Kaneko et al. |
| 5,798,237 | A | * | 8/1998 | Picataggio et al. |
| 6,284,518 | B1 | * | 9/2001 | Henick-Kling et al. |

OTHER PUBLICATIONS

Andersen et al., "Are Growth Rates of *Escherichia coli* in Batch Cultures Limited by Respiration", J. of Bacteriology, 1980, pp. 114–123, vol. 144, No. 1, Univ. of Microbiology, Copenhagen Denmark.

Andersen et al., "Twofold Reduction of Phosphofructokinase Activity in *Lactococcus lactis* Results in Strong Decreases in Growth Rate and in Glycolytic Flux", J. of Bacteriology, 2001, pp. 3458–3467, vol. 183, No. 11, American Society for Microbiology.

Anraku et al., "The Aerobic Respiratory Chain of *Escherichia coli*", TIBS 12, 1987, pp. 262–266, Univ. of Tokyo Hongo, Tokyo Japan.

Atlas, R.M., Principles of Microbiology, 1995, p. 147, Mosby–year Book, Inc., Missouri.

Brock et al., Biology of Microorganisms, Ninth Edition, 2000, Prentice Hall, Upper Saddle River, US.

Bryan–Jones et al., "Haematin–Dependent Oxidative Phosphorylation in *Streptococcus Faecalis*", J. Gen. Microbiol., 1969, pp. 247–260, vol. 58, Printed in Great Britain.

Clarke et al., "The Effect of Haematin and Catalase on *Streoticoccus Faecalis* var. *Zymogenes* Growing on Glycerol", J. of General Microbiology, 1980, pp. 339–347, vol. 121, Printed in Great Britain.

De Ruyter et al., "Controlled Gene Expression Systems for *Lactococcus Lactis* with the Food–Grade Inducer Nisin", Applied & Environmental Microbiology, 1996, pp. 3662–3667, vol. 62, No. 10, American Society for Microbiology.

De Vos et al., "Gene Cloning and Expression Systems in Lactococci", Genetics and Biotechnology of Lactic Acid Bacteria, 1994, pp. 52–105, Blackie Academic & Professional, Glasgow, United Kingdom.

Faust et al., "Phosphorylation Coupled to NADH Oxidation with Fumarate in *Streptococcus Faecalis* 10CI$^1$", Archives of Biochemistry & Biophysics, 1970, pp. 392–398, vol. 137, Cornell Univ., Ithaca, New York.

Foster et al., "Stoichiometry of Subunits in the H$^+$–ATPase Complex of *Escherichia coli*", J. of Biological Chemistry, 1982, pp. 2009–2015, vol. 257, No. 4, Univ. of Wisconsin Medical School, Madison Wisconsin.

Gallin et al., "Evidence for Oxidative Phosphorylation in *Streptococcus Faecallis*", Biochemical & Biophysical Research Communication, 1964, pp. 630–635, vol. 17, No. 6, Cornell Univ., Ithaca, New York.

Gay, "Construction and Characterization of an *Escherichia Coli* Strain wotj a uncl Mutation", J. of Bacteriology, 1984, pp. 820–825, vol. 158, No. 3, American Society for Microbiology.

Ingledew et al., "The Respiratory Chains of *Escherichia Coli*", Microbiological Reviews, 1984, pp. 222–271, vol. 48, American Society for Microbiology.

Ingraham et al., Growth of the Bacterial Cell, 1983, pp. 148–151, Saunderland, Massachusetts: Sinauer Associates, Inc.

Israelsen et al., "Cloning and Partial Characterization of Regulated Promoters from *Lactococcus Lactis* Tn917–lacZ Integrants with the New Promoter Probe Vector, pAK80", Applied Environmental Microbiology, 1995, pp. 2540–2547, vol. 61, No. 7, American Society for Microbiology.

(List continued on next page.)

Primary Examiner—Leon B. Lankford, Jr.
(74) Attorney, Agent, or Firm—Foley & Lardner

(57) ABSTRACT

A method of enhancing biomass yield of a lactic acid bacterial species cell culture, comprising cultivating the cells in a process comprising the steps of providing conditions that results in a reduced glycolytic flux and providing conditions that enable the cells to have, under aerobic conditions, a respiratory metabolism. The increased yield of biomass may be the result of an increased yield of ATP which can be obtained by activating the native ATP synthase activity of the H$^+$-ATPase complex by lowering the ATP/ADP ratio, e.g. by carbon source limitation, and/or by increasing the proton gradient (membrane potential) of the cells, e.g. by enhancing or establishing an electron transport chain which can be achieved by enhancing expression of dehydrogenases or electron transport chain components, by adding to the medium a quinone or porphyrin compound or by enhancing the expression of the H$^+$-ATPase activity.

27 Claims, 2 Drawing Sheets

OTHER PUBLICATIONS

Figure 1:
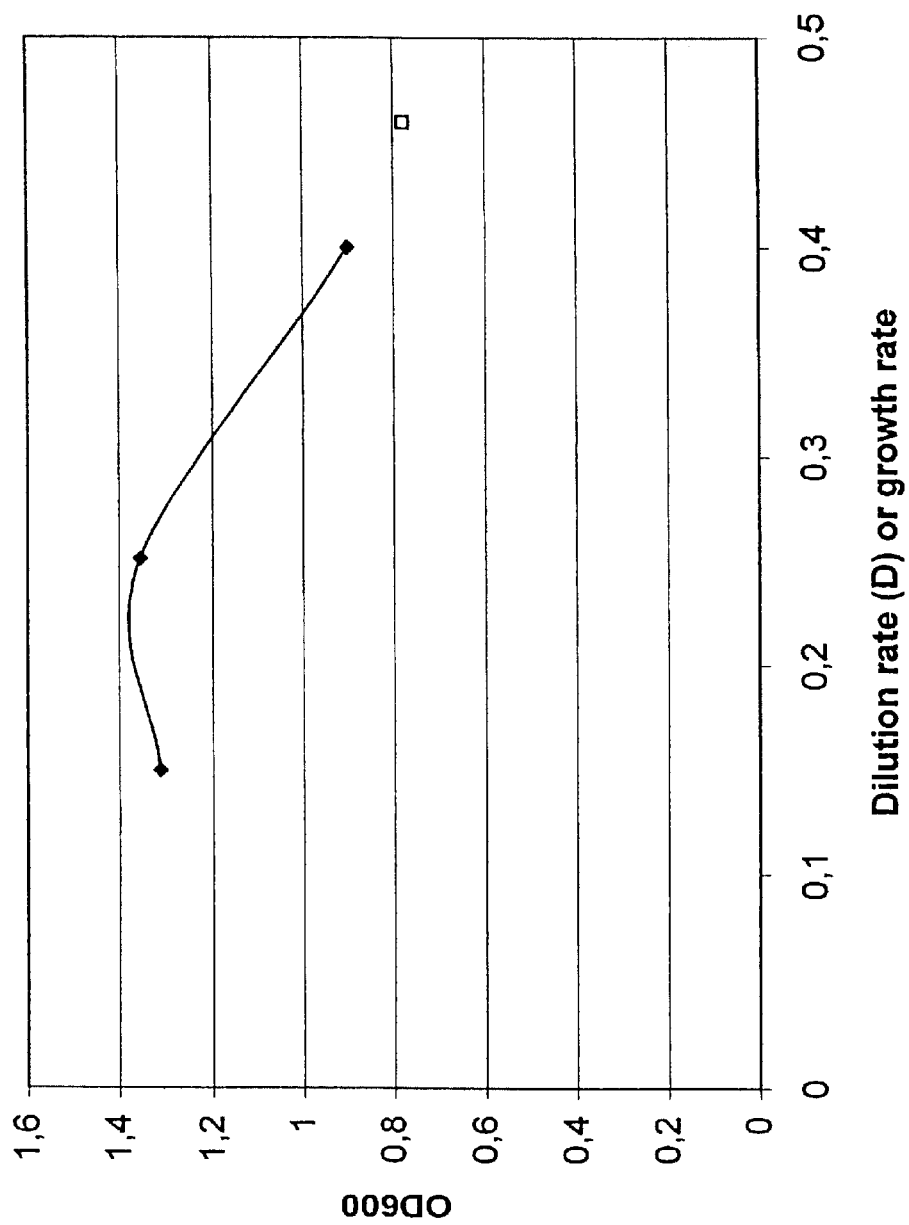

Jensen et al., "Excess Capacity of $H^+$–ATPase and Inverse Respiratory Control in *Escherichia coli*", EMBO Journal, 1993, No. 1277–1282, vol. 12, No. 4, Oxford University Press.

Jensen et al., "Minimal Requirements for Exponential Growth of *Lactococcus Lactis*", Applied Environmental Microbiology, 1993, pp. 4363–4366, vol. 59, No. 12, American Society for Microbiology.

Jensen et al., "The Sequence of Spacers Between the Consensus Sequences Modulates the Strength of Prokaryotic Promoters", Applied Environmental Microbiology, 1998, pp. 82–87, vol. 64, No. 1, American Society for Microbiology.

Kashket, "The Proton Motive Force in Bacteria: A Critical Assessment of Methods", Ann. Rev. Micro., 1985, pp. 219–242, vol. 39, Annual Reviews Inc.

Koebmann et al., "The Membrane–Bound $H^+$–ATPase Complex is Essential for Growth of *Lactococcus Lactis*", J. of Bacteriology, 2000, pp. 4738–4743, vol. 182, No. 17, American Society for Microbiology.

Maloney, "Coupling to an Energized Membrane: Role of Ion–Motive Gradients in the Transduction of Metabolic Energy", *Escherichia Coli* and *Salmonella Typhimurium*, F.C. Neidhardt, ed. 1987, pp. 232–243, American Society for Microbiology.

Poole et al., "Pathways of Electrons to Oxygen", *Escherichia Coli* and *Salmonella Typhimurium*, F.C. Neidhardt, ed. 1987, pp. 170–200, American Society of Microbiology.

Pritchard et al., "Cytochrome Formation, Oxygen–Induced Proton Extrusion and Respiratory Activity in *Streptococcus Faecalis* var. *Zymogenes* Grown in th Presence of Haematin", J. General Microbiology, 1978, pp. 15–22, vol. 104, Printed in Great Britain.

Pugh et al., "Growth of *Streptococcus Faecalis* var. *Zymogenes* on Glycerol: The Effect of Aerobic and Anaerobic Growth in the Presence and Absence of Haematin on Enzyme Synthesis", J. General Microbiology, 1982, pp. 1009–1017, Printed in Great Britain.

Ritchey et al., "Cytochromes in *Streptococcus Faecalis* var. *Zymogenes* Growth in a Haematin–Containing Medium", J. General Microbiology, 1974, pp. 220–228, vol. 85, Printed in Great Britain.

Ritchey et al., "Distribution of Cytochrome–like Respiration in Streptococci", J. General Microbiology, 1976, pp. 195–203, vol. 93, No. 1, Printed in Great Britain.

Smalley et al., "Molar Growth Yields as Evidence for Oxidative Phosphorylation in *Streptococcus Faecalis* Strain $10C1^1$", J. Bacteriology, 1968, pp. 1595–1600, vol. 96, No. 5, American Society for Microbiology.

Sneath et al., "Streptococcus", Bergey's Manual of Systematic Bacteriology, 1986, pp. 1043–1071, vol. 2, Williams & Wilkins.

Unden et al., "Alternative Respiratory Pathways of *Escherichia coli:* Energetics and Transcription Regulation in Response to Electron Acceptors", Biochemica Et Biophysica Acta 1320, 1997, pp. 217–234, Elsevier Science B.V.

Wachenfeldt et al., "Molecular Biology of *Bacillus Subtilis* Cytochromes", FEMS Microbiology Letters 100, 1992, pp. 91–100, Federation of European Microbiological Societies.

Whittenbury, "Hydrogen Peroxide Formation and Catalase Activity in the Lactic Acid Bacteria", J. Gen. Microbiol., 1964, pp. 18–26, vol. 35, Printed in Great Britain.

* cited by examiner

METHOD OF IMPROVING BIOMASS YIELD OF LACTIC ACID BACTERIAL CULTURES

This is a non-provisional application of provisional application Ser. No. 60/216,356 flied Jul. 5, 2000.

FIELD OF INVENTION

The present invention relates generally to the field of cell biomass production. In particular methods are provided whereby the biomass yield of lactic acid bacterial cells can be enhanced by cultivating the cells under conditions where the ATP synthesis is activated.

TECHNICAL BACKGROUND AND PRIOR ART

Lactic acid bacteria are used extensively in the food and feed industry in the manufacturing of fermented products including dairy products such as cheese, yoghurt and butter, meat products, bakery products, wine and vegetable products. Cultures of such bacteria are generally referred to as starter cultures and they impart specific, desired sensory characteristics to various fermented products by performing a number of functions.

When lactic acid bacteria are cultured in milk or any other starting material, the medium becomes acidified as a natural consequence of the bacterial growth. In addition to the production of lactic acid/lactate from citrate, lactose or other sugars several other metabolites such as e.g. acetaldehyde, α-acetolactate, acetoin, acetate, ethanol, carbon dioxide, diacetyl and 2,3-butylene glycol (butanediol) are produced during the growth of the lactic acid bacteria.

In the present context, the expression "lactic acid bacteria" designates a group of Gram positive, catalase negative, non-motile, microaerophilic or anaerobic bacteria which ferment sugar with the production of acids including lactic acid which is normally the predominant acid produced, acetic acid, formic acid and propionic acid. The industrially most useful lactic acid bacteria are found among *Lactococcus* species, *Lactobacillus* species, *Streptococcus* species, *Oenococcus* species, *Leuconostoc* species and *Pediococcus* species.

In addition to their use as starter cultures in the manufacturing of fermented food and feed products, lactic acid bacteria are, due to their GRAS (generally recognised as safe) status, used increasingly as production strains in the manufacturing of metabolites or polypeptides including enzymes and pharmaceutically active compounds such as vaccine components or other immunoreactive compounds.

It is a significant challenge for the industry to produce cultures of lactic acid bacteria in a cost effective manner. As lactic acid bacteria are generally microaerophilic or anaerobic organisms, it is conventional to propagate cultures of these organisms for industrial applications in fermentation vessels under oxygen limited or anaerobic conditions where the cultures ferment the assimilable carbon sources, generally being present in non-limiting amounts, to acids which, however, for the purpose of propagating the cultures, are neutralised by continuously feeding a base to the fermentation medium.

However, this conventional production method is associated with several drawbacks. Firstly, the yield of biomass is generally relatively low, as the fermentative metabolism of sugars or other carbon sources is an energetically inefficient process which typically only leads to the generation of 1–2 moles of ATP per mole of hexose consumed. Secondly, controlling the fermenter propagation process is relatively complex, e.g. necessitating tight control of pH, oxygen and feed of carbon source and thirdly, even if acid produced is continuously neutralised, this production may be inhibitory to growth and may cause damage to the cells being produced leading to suboptimum yield of biomass and viable cells and/or a reduced shelf-life of the commercial starter culture products made from the thus produced lactic acid bacterial cultures.

In addition to attempts to optimise the oxygen-limited propagation conditions, e.g. by optimising the composition of the cultivation medium with a view to possibly increasing the yield of lactic acid bacterial biomass, there have been reported a few attempts to increase biomass yield and quality of starter cultures by propagating the cultures under aerobic conditions, i.e. under conditions without oxygen limitation.

Thus, WO 00/05342 discloses a process for preparing starter cultures of lactic acid bacteria under aerobic conditions in a rich medium comprising a porphyrin compound and it is reported herein that the thus obtained cultures have improved viability and stability.

The present invention provides a completely novel approach to increasing the yield of biomass of a lactic acid bacterial cell culture during aerobic cultivation, which is based on the discovery that it is possible to obtain a substantial enhancement of biomass yield by providing in the cells being propagated an activation of the ATP synthesis, a mechanism which will be explained in details in the following. By applying this approach, the above drawbacks of the conventional methods of propagating lactic acid bacterial cultures are substantially reduced or eliminated and the production costs are significantly reduced.

SUMMARY OF THE INVENTION

Accordingly, the present invention provides a method of obtaining an increased biomass of a lactic acid bacterial cell culture, the yield exceeding that which can be obtained at maximum from substrate level phosphorylation, the method comprising the steps of (i) providing in the cell conditions that results in a reduced glycolytic flux, and (ii) providing conditions that enables the cell under aerobic conditions to have a respiratory metabolism.

As it will be explained in details in the following, an increased biomass yield of a lactic acid bacterial cell culture can be accomplished in several ways including manipulations of the propagation conditions, selection of spontaneously occurring mutants and the use of specific genetic modifications of the strains to be propagated.

In another aspect of the present invention there is provided a method of reducing the content of by-products in a production of biomass of lactic acid bacterial cells, said method comprising of a step of increasing the yield of biomass by (i) providing in the cell conditions that results in a reduced glycolytic flux and (ii) providing conditions that enables the cell under aerobic conditions to have a respiratory metabolism.

In yet another aspect, there are provided lactic acid bacterial cells obtainable by the method according to the invention.

In a further aspect the present invention pertains to a lactic acid bacterial cell produced by culturing the cell under conditions that results in a reduced glycolytic flux, and under conditions that enable the cells to have, under aerobic conditions, a respiratory metabolism, said cell having, relative to a lactic acid bacterial cell produced in the presence of a readily metabolised carbon source in excess, an increased activity of the enzymes involved in the uptake and/or degradation of a that carbon source in which the bacterial cell has been propagated, and containing a detectable amount of a porphyrin compound and/or a cytochrome.

In a still further aspect there is provided a starter culture composition comprising the lactic acid bacterial culture or the lactic acid bacterial cell according to the invention.

DETAILED DISCLOSURE OF THE INVENTION

The primary objective of the present invention is to provide a novel method of enhancing biomass yield of a cell culture of a lactic acid bacterial species, a common feature of which is a propagation process that includes the cultivation of the cell under conditions that results in a reduced glycolytic flux in the cell, and under conditions that enables the cells to have a respiratory metabolism under aerobic conditions. In one preferred embodiment this increased yield of biomass is provided by an increased yield of ATP in the cells which is obtained either by increasing substrate level phosphorylation or by inducing oxidative phosphorylation therein. The terms "substrate level phosphorylation" and "oxidative phosphorylation" and their physiological implications will be explained in details below.

The present invention is based on the surprising findings that an increased yield of ATP resulting in an increased yield of biomass of a lactic acid bacterial cell culture can be provided by cultivating the cells under conditions leading to an increased yield of ATP through substrate level phosphorylation and oxidative phosphorylation. This can be obtained by using different strategies such as combining the growth of cells on a slowly fermentable carbon source with the addition of a porphyrin compound to the growth medium. The slow fermentation rate can also be obtained for readily fermentable carbon sources by growing the cells in the presence of a limiting concentration of the carbon source, e.g. in a chemostat or a fed batch fermenter. The slow fermentation rate can also be obtained by introducing mutations in the cells which cause a lower rate of metabolisation of the carbon source. The increased yield of ATP results in the production of lower amounts of end products per g biomass produced. Therefore, the growth inhibition caused by these products is diminished and an increased biomass concentration can be produced under conditions where the end products are limiting for the cell growth.

It was further found that an additional increase in yield of ATP resulting in an increase in biomass can be provided by activating the native ATP synthase activity of the cells leading to oxidative phosphorylation as it will also be explained in the following. In further embodiments, the increased level of ATP is achieved by increasing in the cells the expression of ATP synthase or by increasing the proton gradient. Any of such manipulations, either separately or in combination, will lead to an increased yield of ATP in the cells via oxidative phosphorylation when the cells are propagated in the presence of a terminal electron acceptor, which in turn will result in an improved biomass yield.

1. Introduction to substrate level phosphorylation and oxidative phosphorylation ATP (adenosine triphosphate) is the universal carrier of free energy in biological systems. It is an energy rich molecule because its triphosphate unit contains two phospho-anhydride bonds ($\Delta G=-7$ kJ/mol). When ATP is hydrolysed to ADP and $P_i$, free energy is released and becomes available for driving the numerous anabolic reactions and other processes that require an input of free energy.

During growth of bacterial cells in the presence of a fermentable carbon source in the growth medium, ATP can be regenerated by such cells in two different ways: (i) substrate-level phosphorylation, where, during glycolysis, a high energy phosphate bond is transferred directly to ADP and (ii) oxidative phosphorylation, where the redox energy obtained from oxidation of substrates is converted to a proton gradient which is subsequently used to drive the phosphorylation of ADP to ATP.

When bacterial cells are cultivated in the absence of an electron acceptor such as e.g. oxygen, i.e. under anaerobic conditions, or in the absence of a respiratory chain (see below), only substrate level phosphorylation is possible. The proton motive force is then maintained by the $H^+$-ATPase, by coupling the hydrolysis of ATP to translocation of protons across the cytoplasmic membrane, the latter process being driven by energy generated by consumption of ATP being hydrolysed to ADP. As a result hereof, the growth yield (in terms of g dry weightmole substrate) of the bacterial cells is greatly reduced, and most of the carbon and energy source fed is recovered as by-products (Ingraham et al., 1983).

Depending on the organism in question, the carbon source and the conditions for growth, different amounts of ATP are obtained by substrate level phosphorylation. When the growth medium for lactic acid bacteria are supplemented with an excess of glucose or lactose, fermentation is usually homolactic, i.e. mainly lactate is produced. When lactose in the medium is replaced with a less readily fermentable carbon source, or if lactose is fed to the culture at a slow rate, the fermentation shifts to a so-called mixed acid production where acetate, formate, ethanol and lactate are produced, depending on the growth conditions. The number of moles of ATP synthesised per mole of sugar consumed can be estimated directly from the amount of by-products excreted to the growth medium, assuming that the pathways for degradation for the particular organism are known. The part of the sugar which is converted and excreted as lactate results in 2 moles of ATP generated per mole of glucose. The part of the sugar which is converted and excreted as acetate results in 4 moles of ATP generated per mole of glucose. Under aerobic conditions sugar can also be converted to acetoin and this process results in two moles of ATP per mole of glucose converted into acetoin.

When an electron acceptor like oxygen or nitrate is present, certain bacteria such as *E. coli* generates ATP both via substrate-level phosphorylation and oxidative phosphorylation, and under these conditions the growth rate and biomass yield is substantially higher than the case would be in the absence of an electron acceptor. In the presence of an electron acceptor, only a small proportion of the carbon input is recovered as by-products (Andersen and von Meyenburg, 1980).

ATP synthesis by oxidative phosphorylation in mitochondria and bacterial cells can be divided into two steps: (i) generation of an electrochemical gradient of $H^+$ across the membrane (proton motive force) by coupling of the oxidation of e.g. NADH to the translocation of protons across the cytoplasmic membrane. This process is catalysed by the Electron Transport System (ETS) also referred to as the respiratory chains (see more details below); (ii) synthesis of ATP from ADP and $P_i$, catalysed by the membrane bound $H^+$-ATPase, using the proton gradient to drive the endergonic ATP synthesis.

2. Electron transport chains

In bacterial cells and mitochondria respiratory chains couple the oxidation of organic substrates to the translocation of protons across the cytoplasmic membrane. The resulting electrochemical proton gradient is then utilised to drive ATP synthesis, solute uptake maintenance of ion gradients and other energy requiring membrane associated processes.

The enzyme complexes constituting the electron transport chains of bacteria are quite diverse (for a general review on the subject in *E. coli,* see Unden and Bongaerts (1997)). In general, the chains consist of primary dehydrogenases and terminal oxidases which are linked for the purposes of electron transport by a quinone (i.e. ubiquinone, menaquinone or demethylmenaquinone).

The individual respiratory chains differ by their substrates, their intermediary components and their terminal electron acceptors.

Primary dehydrogenases

The primary dehydrogenases include: NADH dehydrogenase, formate dehydrogenase, succinate dehydrogenase, glycerol-3-phosphate dehydrogenase, hydrogenase and lactate dehydrogenase. The function of these components is to transfer electrons from an organic compound (e.g. NADH or succinate) to a quinone. In the case of NADH dehydrogenase, formate dehydrogenase and hydrogenase the electron transfer is coupled to translocation of protons from the cytoplasm to the periplasm. This process is referred to as site I activity (Poole and Ingledew, 1987).

Intermediary components of dehydrogenases

Three quinones are synthesised by *E. coli,* i.e. ubiqinone, menaquinone and dimethylmenaquinone. They are low molecular weight and lipid soluble molecules. Depending on the substrate and electron acceptor in use (and the concentration of oxygen) the membrane content of quinone compounds changes (Ingledew and Poole, 1984). The quinones are believed to function as mobile carriers of electrons (hydrogen atoms) between the large and relatively slow moving dehydrogenases and the terminal oxidases. The reduced form of a quinone is a quinol.

Terminal oxidases

In aerobically grown bacterial cells such as *E. coli* cells, cytochrome $bo_3$ and cytochrome bd are probably (Poole and Ingledew, 1987) the only cytochrome oxidase complexes present. The function of the oxidase complexes is to receive a pair of electrons (hydrogen atoms) from quinol (see above) and transfer these to the terminal electron acceptor ($O_2$) with the concomitant extrusion of two protons (Anraku and Gennis, 1987). This process is referred to as site II activity. The best molecule to function as the final electron acceptor is $O_2$, but molecules like $NO_3^-$ and fumarate can also function as acceptor.

The expression level of both the dehydrogenases and terminal oxidases is regulated by the terminal electron acceptors, where the more preferred electron acceptor tends to repress the terminal oxidases for less preferred electron acceptors. Theoretically, maximum energy conservation is obtained with NADH as the substrate and $O_2$ as the terminal electron acceptor, and minimal energy conservation with e.g. lactate as substrate and fumarate as electron acceptor. To some extent, this regulation favours pathways with high ATP yields. However, under completely aerobic growth conditions, the uncoupled dehydrogenases appear to be used preferentially, which probably reflects that the expression of the components of the respiratory chains is optimised for high flux rather than high ATP yield.

$H^+/e^-$ stoichiometry of the electron transport chains

The enzymes in the electron transport chains show great variability in energy conservation. Energy is conserved by proton pumps, or by arrangement of substrate sites on opposite sides of the membrane resulting in a net separation of charge. In *E. coli* cells the $H^+:e^-$ ratios are between 0 and 4 for the overall electron transport chains depending on the particular enzymes involved.

The electron transfer reaction can be illustrated as follows: two electrons are transferred from a reduced substrate, e.g. NADH to ubiquinone-8 (Q). In *E. coli* cells this process is catalysed by either of two NADH dehydrogenases: NuoA-N which contributes to the proton gradient by two $H^+/e^-$ (site I activity) or Ndh, the activity of which does not result in the release of protons. The quinol that is generated then diffuses within the membrane to either of the terminal oxidases. If this is the cyt $bo_3$ oxidase, then ubiquinol-8 is oxidised at a site near the periplasmic surface of the membrane and two $H^+/e^-$ are released to the periplasm (one $H^+$ due to proton pumping activity and one $H^+$ due to the scalar protons involved (see Unden and Bongaerts, 1997). If the cyt bd oxidase is used, then only one $H^+/e^-$ is released. These numbers reflect the fact that the so-called $bc_1$ complex which increases the efficiency of respiration is not found in *E. coli,* in contrast to other bacteria such as *Bacillus* and *Paracoccus* species. The $bc_1$ complex acts as an extra component between the quinones and the terminal cyt $aa_3$ oxidases in these organism, and results in one additional $H^+/e^-$.

3. The $H^+$-ATPase/ATP synthase complex

Structure and localisation

The $H^+$-ATPase/ATP synthase complex of bacteria is located on the inside of the cytoplasmic membrane. Based on function and localisation, the complex is divided into two parts: $F_1$ and $F_0$. In *E. coli, the $F_1$* part is seen on electron micrographs as 9 nm diameter knobs on the inside of the cytoplasmic membrane, attached to the membrane by narrow stalks. $F_1$ is composed of the five subunits, $\alpha, \beta, \gamma, \delta$ and $\epsilon$ in order of decreasing molecular weight, and the subunit stoichiometry, $\alpha_3\beta_3\gamma\delta\epsilon$ has been established (Foster and Fillingame, 1982). The catalytic site(s) for ATP synthesis and hydrolysis, respectively is located on $F_1$.

The $F_0$ part is embedded in the membrane and binds $F_1$ to the membrane. Without $F_1$ bound, $F_0$ forms a specific proton-conducting channel. The $F_0$ part of the ATP synthase consists of three subunits: a, b and c. The stoichiometry of subunits in the $F_0$ part has been proposed to be $a_1, b_2, c_{8-12}$ (Foster and Fillingame, 1982).

Function of the $H^+$-ATPase/ATP synthase complex

In *E. coli,* the $H^+$-ATPase/ATP synthase couples the synthesis or hydrolysis of ATP to the translocation of protons across the cytoplasmic membrane. Under aerobic conditions, the proton motive force generated by the respiratory system is used by the ATP synthase to drive the energy requiring ATP synthesis and to maintain solute gradients. Under anaerobic conditions, the proton motive force can be generated by the complex through hydrolysis of ATP.

$H^+$/ATP stoichiometry of the $H^+$-ATPase/ATP synthase

The number of protons utilised by the $H^+$-ATPase/ATP synthase to generate one molecule of ATP ($nH^+$/ATP) and the number of protons which is translocated per molecule of ATP that is hydrolysed (anaerobic growth) has been disputed. In case of aerobic cells the thermodynamic inequality, $$n^*\Delta p > \Delta G_P/F$$

must be fulfilled, where n is the stoichiometry, $\Delta p$ is the proton motive force (mV), $\Delta G_{ATP}$ is the free energy of reaction I (−30 kJ/mole from right to left) and F is Faradays constant (96.519 J). In *E. coli* the value of $\Delta p$ is 165 mV at $pH_{out}$=7.3 (Kashket 1985), which means that the value of n must be at least 1.9. Therefore, a stoichiometry of 2 $H^+$/ATP would probably be too small to overcome the energy of activation and a value of 3 $H^+$/ATP seems more likely and is in good agreement with experimental results (Maloney 1987). The value of n, however, is not necessarily an integer, but an integer would be easier to combine with the mechanism suggested for ATP synthesis.

The genes encoding the $H^+$-ATPase/ATP synthase in bacteria

The eight genes, which encode the $(F_1F_0)$ $H^+$-ATPase/ATP synthase (in the following also referred to only as $H^+$-ATPase) in *Lactococcus lactis subsp. cremoris* MG1 363 have been cloned and sequenced (Koebmann et al., 2000). The deduced amino acid sequences of the corresponding $H^+$-ATPase subunits showed significant homology with the subunits from other organisms, particularly the subunits that form the $F_1$ part of the complex.

The genes are organised in an operon with the gene order atpEBFHAGDC, i.e. the order of atpE and atpB are reversed with respect to the more typical bacterial organisation found in e.g. *E. coli, B. subtilis* and *E faecalis*. The functional implications, if any, of this gene reversal in *L. lactis* is not clear but could reflect the fact that the $H^+$-ATPase acts as a proton pump rather than as an ATP generating enzyme.

In many bacteria such as *E. coli* the atp operon starts with the gene atpI as the first structural gene, but such a gene appears to be absent in *L. lactis* and other lactic acid bacteria. The function of the polypeptide encoded by the atpI in these organisms is unknown; the polypeptide is not an essential part of the $H^+$-ATPase complex, but deletion of the atpI gene has been demonstrated to affect the ability of the $H^+$-ATPase to generate ATP under aerobic conditions (Gay, 1984).

Therefore, the absence of the atpI gene in *L. lactis* and other lactic acid bacterial species may reflect the fact that the enzyme is acting as a proton pump rather than as an ATP synthesising enzyme under normal growth conditions.

4. Evidence for electron transport chains in bacteria related to Lactococcus

Cells of *Lactococcus* species (*lactococci*) are generally considered to be facultative anaerobes, devoid of a functional electron transport chain, i.e. the cells are exclusively relying on substrate level phosphorylation (Brock et al, 2000; Atlas, 1995; Sneath et al., 1986). However, for several related bacterial species (*Enterococcus faecalis* and its variants *liquefaciens* and *zymogenes*) evidence is found in the literature that the addition of haemin (i.e. an iron-containing protoporphyrin which is a prostethic group of cytochromes) to growth media reconstitutes an electron transport chain. As early as 1964, Whittenbury reported the presence of $a_2$ and b type cytochromes in *E. faecalis* strain H69D5 when it was cultivated in a medium supplemented with heated blood. A subsequent paper from the same group reported the presence of a $b_2$ type cytochrome in membrane fractions of *Enterococcus faecalis* strain 581 when this strain was cultivated in a medium supplemented with haemin (Bryan-Jones and Whittenbury, 1969). Another research group reported oxidative phosphorylation in *E. faecalis* by NADH oxidation of membrane fractions and indirectly by molar growth yields of strain IOCI (Gallin and VanDemark, 1964; Smalley et al, 1968; Faust, 1970). These latter investigators, however, did not supplement their media with haemin or any blood derivative and a publication by Bryan-Jones and Whittenbury (1969) could not confirm their findings.

Ritchey and Seeley, (1976) screened 134 *Enterococcus/Streptococcus/Lactococcus* strains by inhibition of electron transport as well as the cellular site of NADH oxidation. Each strain was placed into one of the following groups: strains having cytochrome-like NADH oxidase, strains having flavin-like NADH oxidase and strains having no NADH oxidase activity. Most of the *Enterococcus* strains exhibited cytochrome-like activity whereas only 3 out of the 9 tested *Lactococcus* strains fell into this group.

However, no attempts to show either increased biomass or increased proton export in the above 134 strains were made.

A more detailed report (Pritchard and Wimpenny, 1978) could confirm the ability of an *Enterococcus* strain (designated TR) to establish a functional cytochrome system and these authors showed that the transport of electrons to oxygen is coupled to proton translocation. Later, *E. faecalis* was investigated for its change in enzyme synthesis when grown anaerobically or aerobically, respectively on glycerol in the presence/absence of haemin. The proton transport in response to oxygen pulses was directly measured (Clarke and Knowles, 1980; Pugh and Knowles, 1982) in those cells.

5. Calculation of contributions from substrate level Phosphorylation and oxidative phosphorylation to overall ATP synthesis Whether or not a bacterial cell can benefit from oxidative phosphorylation during growth can be estimated from the yield of biomass obtained per mole of sugar consumed as follows: total ATP production is estimated from the final yield of biomass, ATP produced by substrate-level phosphorylation is calculated from the composition of by-products (see above), and the ATP production through oxidative phosphorylation is then calculated as the difference between the two former ATP values. Ritchey and Seeley (1974) found that the aerobic biomass yield of *Enterococcus* (previously *Streptococcus*) *faecalis* increased from 40.6 to 50.8 g dry weight/mole glucose and since almost all carbon ends up in acetate these authors calculated that about 1 mole of ATP per mole of glucose was generated by oxidative phosphorylation when *E. faecalis* was cultivated aerobically in the presence of a haeme source. However, the present inventors consider this reported increase in biomass yield to be at least partially due to savings of ATP that would otherwise have been spent on proton pumping activity of the $H^+$-ATPase.

It can therefore be concluded from the prior art that no reports are available that could suggest that the biomass yield of non-pathogenic, industrially useful lactic acid bacteria can be increased by cultivating such bacteria under conditions where the biomass yield exceeds that which can be obtained at maximum from substrate level phosphorylation. Thus, nowhere in the prior art is it disclosed that the cultivation of lactic acid bacteria under conditions where substrate level phosphorylation and/or oxidative phosphorylation are established results in an increased yield of ATP which in turn leads to a significant increase of biomass yield. Accordingly, in one preferred embodiment, the increased biomass yield is obtained by an increased yield of ATP. In preferred embodiments, the method is one wherein the increased yield of ATP, i.e. the yield of ATP which exceeds that which can be obtained at maximum from substrate level phosphorylation, is at least ½ ATP, such at least 1 ATP, e.g. at least 2 ATP, including at least 3 ATP, such as at least 4 ATP, e.g. at least 5 ATP, including at least 6 ATP, such as at least 8 ATP, e.g. at least 10 ATP, including at least 12 ATP.

In the present context, the term "biomass" relates to the amount of a given cell culture, i.e. any organism or living cell growing in a medium, that is actively growing. In general, the biomass yield of a cell culture is presented as gram biomass obtained per litre culture medium.

In accordance with the present invention, the yield of biomass obtained by the present method exceeds that which can be obtained at maximum from substrate level phosphorylation. The expression "yield that exceeds that which can be obtained at maximum from substrate level phosphorylation" relates, in the present context, to the yield of biomass which can be expected under the given growth conditions, as explained in details above.

In preferred embodiments, the increased biomass yield obtained by the method according to the invention is at least 10% higher than the biomass yield of the same lactic acid bacterial cell culture obtained when culturing the cell under aerobic or anaerobic conditions where lactose or glucose are in excess, such as at least 20% higher, e.g. at least 30% higher, including at least 40% higher, such as at least 50% higher, e.g. at least 60% higher, including at least 70% higher, such as at least 80% higher, e.g. at least 90% higher or even at least 100% higher. However, in further useful embodiments, the method is one wherein the increased biomass yield is at least 120% higher than the biomass yield of the same lactic acid bacterial cell culture obtained when culturing the cell under aerobic or anaerobic conditions where lactose or glucose are in excess, such as at least 150% higher, e.g. at least 175% higher, including at least 200% higher, such as at least 250% higher, e.g. at least 300% higher, including at least 350% higher, such as at least 400% higher, e.g. at least 500% higher or even at least 600% higher.

In one useful embodiment, the increased yield of ATP is provided by activating the native ATP synthase activity in the cells, i.e. providing conditions where the activity of the $H^+$-ATPase/ATP synthase complex is directed towards ATP synthesis or by enhancing the expression of the ATP synthase of the cell. There are several ways whereby the ATP synthase activity of lactic acid bacterial cells can be activated. One of these ways is to reduce the intracellular concentration of ATP or to increase the intracellular concentration of ADP, or in other words, to reduce the ATP/ADP ratio, one implication hereof being that the level of substrate for the ATP synthase (ADP) is increased, while the product (ATP) is decreased, which in turn leads to an increase of the intracellular ATP pool. Another way, which is explained in details below, is to increase the ATP synthase activity by increasing the proton gradient of the cell.

In lactic acid bacteria the sugar flux through the cells is almost exclusively a catabolic flux, i.e. the flux that supplies the ATP required for growth. In one preferred embodiment, a lowered ATP/ADP ratio is provided by the reduced glycolytic flux in step (i) of the method according to the invention. In the present context, the expression "glycolytic flux" relates to the consumption of a given carbon source per unit of time per gram biomass, i.e. e.g. mmole glucose/h/g biomass. Accordingly, the expression "reduced glycolytic flux" relates to a flux in a cell which is reduced relative to the flux in cells cultivated under aerobic conditions in the presence of a porphyrin compound and in excess amounts of lactose or glucose.

Such a reduced glycolytic flux in the cell can be provided by cultivating the lactic acid bacterial cells aerobically under carbon source limitation so as to suppress or reduce glycolysis. These conditions can be achieved by using as the carbon source, a sugar that is not assimilated readily by the particular lactic acid bacteria such as it is shown in the below examples. Glucose and lactose are the sugars preferentially metabolised by lactic acid bacteria. Accordingly, in the present context, any carbon source that is not glucose or lactose are considered as not being readily assimilated by lactic acid bacteria. Such sugars include monosaccharides, such as pentoses, e.g. ribose, xylose, arabinose, hexoses other than glucose, e.g. allose, mannose, gulose, idose, galactose, talose; disaccharides other than lactose such as e.g. maltose; trisaccharides and polysaccharides.

Another approach to changing the rate of ATP synthesis in the lactic acid bacterial cells is to change the concentration of the sugar substrate in the growth medium, e.g. by cultivating the cells in a fed-batch culture or a chemostat culture. In such a culture, sugar is gradually added to the culture while the cells are growing, which has the effect that the cells can be constantly starved for sugar. The growth will thus be slower than if the sugar concentration was present in excess and the ATP/ADP ratio in the growing cells will be lower as compared to cultivating the cells under conditions without carbon source limitation. Any sugar that can be metabolised by the organism in question could in principle be used for this purpose, e.g. glucose, maltose, galactose and lactose and other sugars as mentioned above.

Accordingly, in a useful embodiment, the method of the invention is one wherein the ATP synthase activity of the cells is activated by reducing the glycolytic flux in the cell and thus reducing the ATP/ADP ratio by cultivating the cells under carbon source limitation conditions which can be established either by using a carbon source which is not as readily metabolised by the cells as are glucose and lactose and/or by cultivating, at least during part of the cultivation or propagation period, the cells under growth-limiting concentrations of the carbon source such as under fed batch conditions and/or continues conditions. It is contemplated that a propagation process comprising alternate fed batch conditions and continuos sugar feeding conditions can be used to achieve a reduction of the ATP/ADP ratio and thereby driving the ATP synthesis under oxidative phosphorylation conditions.

An alternative way to obtaining a reduced glycolytic flux in the cells and thus a low ATP/ADP ratio is to modify the capacity for sugar transport or glycolysis. The glycolytic flux in living cells and accordingly, the rate of ATP synthesis, can be lowered by affecting one or more of the steps in the pathways that degrade the sugar and generate ATP. In the case of starter cultures for the dairy industry, it may be preferred to change the capacity for uptake and/or degradation of sugars other than lactose, so that the properties of the starter culture is unaffected. This can e.g. be obtained by constructing or directly selecting mutants which have a lower capacity for sugar transport or sugar specific reactions, or both. In the case of maltose, one convenient way to achieve a reduction of both of these enzyme activities is to construct or select a mutant with a lower expression of maIR which is an activator of the expression of the maltose degrading enzymes. Similarly, the enzymes involved in galactose uptake and/or degradation can be modified. Accordingly, in a useful embodiment of the present invention, the carbon source limiting conditions are provided by modifying the cell in order to assimilate the carbon source at a lower rate relative to its parent strain.

It will be appreciated by the person of skill in the art that the above approaches to reduce the ATP/ADP ratio can be combined.

In a further embodiment, the increased level of ATP in the cells is provided by increasing the expression of the genes coding for ATP synthase. It will be appreciated by the person of skill in the art that such an enhanced expression of one or more of the genes of the $H^+$-ATPase/ATP synthase complex can be achieved in several ways using recombinant DNA techniques which are known per se. Thus, the expression can be increased by introducing in the cells additional copies of the gene(s) or by inserting one or more regulatory sequences that enhance(s) expression, such as e.g. a promoter that is stronger than the native promoter and which e.g. can be inserted upstream of the atp operon, either by gene replacement or by selection, or by inserting one or more sequences that reduce(s) or inhibit(s) any inhibition of the ATP synthase. Accordingly, in an useful embodiment, the expression of ATP synthase is increased by inserting a regulatory sequence that enhances expression or by reducing or relieving inhibition of the expression of ATP synthase.

It has been shown that the activity of the H+ATPase/ATP synthase is subject to regulation for instance by low pH. Therefore, another option is to activate this mechanism by selecting mutants or by genetic modifications of the cells.

As it is mentioned above, the H+ATPase/ATP synthase complex in lactic acid bacteria is capable of ATP synthesis in vitro, and as it is demonstrated in the below examples, it can also generate ATP in the growing cell. However, the usual role of the enzyme is the opposite in these organisms, and it is therefore possible that the enzyme is not quite optimal for working in the direction of ATP synthesis. The lactic acid bacterial enzyme appears to differ most from that of aerobic organisms in the $F_0$ part, where the homology of the subunits to those of the enzyme of aerobic bacteria is lowest. Also, the fact that the operon lacks the atpl gene which is well conserved among the aerobic organisms, as it is discussed above, indicates that there could be room for improvement of the ATP synthase activity of the enzyme. Therefore, it is contemplated that replacement of particular $F_0$ subunits of the lactic acid bacterial enzyme complex with subunits from e.g. aerobic organisms may result in increased ATP synthesis. Furthermore, inserting and expressing an atpl gene that is missing in lactic acid bacteria as a means of enhancing ATP synthase activity is contemplated.

In accordance with a further step of the method according to invention, the enhanced biomass yield of the lactic acid bacterial cell culture is obtained by providing in step (ii) conditions that enable the cells under aerobic conditions to have a respiratory metabolism. In the present context, the expression "enable the cells under aerobic conditions to have a respiratory metabolism" relates to conditions where the lactic acid bacterial cells under aerobic condition is capable of coupling the oxidation of organic substances to an electron transport chain such that the electrons are transferred to oxygen. Such conditions can be provided as explained in details below.

Accordingly, one approach to obtaining an increased biomass yield of a lactic acid bacterial cell culture resulting e.g. from an increased yield of intracellular ATP, is to increase the proton gradient of the cells, as an increased proton gradient will lead to an increased ATP synthase activity via oxidative phosphorylation. Accordingly, in a further embodiment the method of the invention is one wherein the ATP synthase activity is activated by increasing the proton gradient.

One general approach to increasing the proton gradient of the lactic acid bacterial cells is to enhance the function of any of the elements in the electron transport chain as described above that may be naturally present in such cells or to insert or introduce any such elements that are not naturally present in lactic acid bacteria. Thus, e.g. when such missing elements are enzymes, genes that code for such enzymes can be isolated from organisms where they are naturally present, and inserted in the lactic acid bacterial cells. Thus, in a useful embodiment, the proton gradient is increased by increasing the expression of the native components of the electron transport chain.

Accordingly, the proton gradient (membrane potential) in a lactic acid bacterial cell can be increased by providing in the cells the expression of a dehydrogenase including any of the primary dehydrogenases as are mentioned above, i.e. NADH dehydrogenase, formate dehydrogenase, succinate dehydrogenase, glycerol-3-phosphate dehydrogenase, hydrogenase and/or lactate dehydrogenase. In organisms where genes coding for any of such dehydrogenases are naturally present, their expression can be enhanced by any of the means mentioned above for ATP synthase, or where any of such dehydrogenase coding genes are not naturally present, it or they can be inserted and expressed.

An alternative approach to increasing the proton gradient is to reduce or eliminate the expression of a $NAD^+$ regenerating enzyme activity such as the expression of NADH oxidase activity. The person of skill in the art will appreciate that this can be achieved by recombinant DNA techniques leading to inactivation of the gene coding for $NAD^+$ regenerating enzyme activity such as mutation(s) in the coding sequence or by deleting the coding sequence e.g. by recombinant DNA techniques.

Accordingly, in useful embodiments, the method is one wherein the proton gradient is increased by increasing expression of a dehydrogenase including NADH dehydrogenase, or by reducing or eliminating the expression of a $NAD^+$ regenerating enzyme activity such as NADH oxidase activity.

Another way to increase the rate of ATP synthesis by oxidative phosphorylation is to increase the efficiency of terminal oxidase of the respiratory chains. This can be done by introduction of heterologous respiratory chain components from other organisms, either on a plasmid or on the chromosome. Some of the candidates for this are the cytochrome $bo_3$ type from e.g. *E. coli*, or the $aa_3$ type, alone or together with cyt $bc_1$ complex from e.g. *B. subtilis*. Accordingly, in a useful embodiment, the proton gradient is increased by increasing the expression of the endogenous cytochromes including cytochrome bd. In further embodiments, method is one where the proton gradient is increased by introducing a heterologous respiratory chain component such as a cytochrome selected from the group consisting of cytochrome type $bo_3$, cytochrome type $aa_3$ and cytochrome complex cyt $bc_1$.

In the present context the term "cytochrome" relates to a group of electron-transporting proteins containing a haeme prosthestic group and thus to components of the respiratory and photosynthetic electron transport chains, in which the haeme ion exits in oxidised or reduced state. The definition encompasses, but is not limited to, cytochromes of a-, b-, c-, d- or o-types and combinations of these cytochrome types as e.g. mentioned in Wachenfeldt & Hederstedt (1992). It will be understood, that the term "the respiratory electron transport chain" refers to either an aerobic respiratory electron transport chain functioning with molecular oxygen as terminal electron acceptor, or an anaerobic respiratory electron transport chain functioning with other terminal electron acceptors than molecular oxygen such as nitrate, sulphate, fumarate or trimethylamine oxide.

Additionally, the efficiency of the respiratory chain, and accordingly the proton gradient, can be enhanced by cultivating the lactic acid bacterial cells in a medium containing a quinone, a porphyrin compound and/or a cytochrome or by cultivating the cells under conditions which favour the formation of a quinone, a porphyrin compound and/or a cytochrome. In this context, useful quinones include those mentioned above. "Porphyrin compounds" refers in the present context to cyclic tetrapyrrole derivatives whose structures are derived from that of porphyrin by substitution of the carbons located at the apices of the pyrrole core, by various functional groups. It also refers to complexes of said derivatives with a metal atom that forms co-ordinate bonds with two of the four nitrogens of the porphyrin ring. The definition encompasses also, but is not limited to, uroporphyrins, coproporphyrins, protoporphyrins and haematoporphyrins including their salts and esters and their complexes with a metal atom, preferably an iron atom, the dihydrochloride of coproporphyrin I, the tetraethyl ester of coproporphyrin II, the disodium salt of protoporphyrin IX, the dichloride of haematoporphyrin IX, the tetraisopropyl ester or the tetramethyl ester of coproporphyrin, the tetraisopropyl ester or the tetramethyl ester of coproporphyrin III, haematoporphyrin IX, haemoglobin, protoporphyrin IX, the dimethyl ester of protoporphyrin IX, zinc protoporphyrin IX, haematin and cytohaemin. Particularly preferred porphyrin compounds are protoporphyrin IX and its complexes with an ion atom, in particular haeme and haemin. Furthermore, the definition encompasses various chlorophylls, such as chlorophyll a and chlorophyll b, their derivatives such as chlorophyllins and also their salts and esters, and their complexes with a metal atom, such as an iron, copper or magnesium atom.

As it is mentioned above, lactic acid bacteria are, in addition to their use in food and feed fermentation processes, used as production organisms for various gene products including pharmaceutically active products. The present method is applicable in processes where a recombinant lactic acid bacterial cells are cells comprising gene(s) coding for a desired gene product, as it may in such processes be advantageous to first provide a dense culture of such cells before the gene coding for a desired gene product is actually expressed. In a useful embodiment, the expression of the gene is under the control of an inducible or a constitutive promoter. In accordance with the invention, an interesting embodiment is a method where the biomass comprises cells comprising a gene coding for a desired gene product located on a replicon that is incapable of replication under a first set of conditions, but which is capable of replicating under a second set of conditions, the method comprising that the cells are cultivated in a first cultivation phase under the first set of conditions to produce the biomass followed by changing to the second set of conditions to obtain replication of the replicon. In this embodiment, the cells are propagated in the first cultivation phase under aerobic conditions leading to an increase of the ATP yield via oxidative phosphorylation and leading to suppression of the expression of the gene coding for a desired gene product, whereas in the second cultivation phase, the conditions are shifted to provide for expression of the coding gene. In preferred embodiments, the desired gene product that is encoded is selected from the group consisting of an enzyme such as a milk clotting enzyme including a chymosin species or a microbially derived protease, and a pharmaceutically active gene product.

In any of the above embodiments, the cell is preferably of a lactic acid bacterial species selected from the group consisting of a *Lactococcus* species, a *Streptococcus* species, a *Leuconostoc* species, a *Lactobacillus* species, a *Pediococcus* species and an *Oenococcus* species. Additionally, it is contemplated that cells of a *Bifidobacterium* species, which are taxonomically unrelated to lactic acid bacteria, but which, based on functional similarities with the lactic acid bacteria, are traditionally included in this group, can be used in the present method.

An important objective of the present invention is to provide a cost effective manner of producing a lactic acid bacterial biomass which can be used for the manufacturing of food or feed starter culture. This implies that the cell biomass after propagation is subjected to conventional downstream processing steps, typically including harvesting of cells, e.g. by centrifugation, freezing and/or freeze-drying and packaging.

From the description of the above method it is evident that the production of the biomass of the lactic acid bacterial cell culture involves a decreased production of by-products. One explanation may be that the presence of an electron acceptor results in that only a small proportion of the carbon input is recovered as by-products. Accordingly, in a further aspect of the present invention there is also provided a method of reducing the content of by-products in a production of biomass of lactic acid bacterial cell cultures said method comprising the steps of (i) providing in the cell conditions that result in a reduced glycolytic flux and (ii) providing conditions that enables the cell to have a respiratory metabolism under aerobic conditions.

Microorganisms will normally adjust the expression of their metabolic genes according to which enzymes are required under a given set of growth conditions. Thus, when e.g. using maltose as a carbon source, the genes involved in maltose uptake and maltose degradation will be expressed whereas the lactose genes will be repressed, and vice versa when lactose is the carbon source. Therefore, if a lactic acid bacterial cell culture, which in accordance with the method of the present invention has been grown in the presence of maltose, i.e. a not readily metabolised carbon source, and under conditions that enable the cells to have, under aerobic conditions, a respiratory metabolism, will clearly, relative to a cell produced in the presence of a readily metabolised carbon source in excess, have an increased activity of the enzymes involved in the uptake and/or degradation of that carbon source in which the bacterial cell has been propagated, and containing a detectable amount of a porphyrin compound and/or a cytochrome. It will be understood, that a person skilled in the art knows how to determine this increased activity of the enzymes and how to determine the presence of a porphyrin compound or a cytochrome. Accordingly, the present invention provides in a further aspect a lactic acid bacterial cell obtainable by the method according to the invention.

In a still further aspect, there is provided a lactic acid bacterial cell produced by culturing the cell under conditions as described above that results in a reduced glycolytic flux, and under conditions that enable the cells to have, under aerobic conditions, a respiratory metabolism, said cell having, relative to a lactic acid bacterial cell produced in the presence of a readily metabolised carbon source in excess, an increased activity of the enzymes involved in the uptake and/or degradation of a that carbon source in which the bacterial cell has been propagated, and containing a detectable amount of a porphyrin compound and/or a cytochrome.

Further to the discussion above, a lactic acid bacterial cell produced in the presence of e.g. maltose which subsequently is provided with lactose as the carbon/energy source, will not be able to restart growth immediately, because the genes involved in maltose uptake and maltose degradation will be expressed whereas the lactose genes will be repressed. This situation may for instance take place if a starter culture has been cultivated in the accordance with the method of the present invention in the presence of maltose and is subsequently inoculated into milk in order to acidify the milk. At the time of inoculation, the culture needs to turn on the lactose specific genes first which results in a lag-phase for growth and acid production. As it is shown in the below Examples, it is e.g. possible to achieve induction of expression of the lactose genes by growing the cells on galactose or by cultivating the cell in a fed batch or chemostat set up where lactose is present in such low concentrations. Thus, in one useful embodiment, the lactic acid bacterial cell is one which constitutively expresses the lac operon and/or gal operon. Such constitutive expression can e.g. be provided by a mutation in the gene coding for the lac repressor and/or lac operator using known techniques in the art.

As mentioned above, it is possible to detect the presence and the amount of a porphyrin compound in cells which have been cultured in the presence of a porphyrin compound. Thus, in a preferred embodiment, the lactic acid bacterial cell according to the invention contains at least 0.1 ppm on a dry matter basis of a porphyrin compound, including at least 0.2 ppm, such as at least 0.5 ppm, including at least 1 ppm, e.g. at least 2 ppm, such as at least 5 ppm, including such as 10 ppm, such as at least 20 ppm, e.g. at least 30 ppm, such as at least 40 ppm, e.g. at least 50 ppm, such as at least 60 ppm, e.g. at least 70 ppm, such as at least 80 ppm, e.g. at least 90 ppm, such as at least 100 ppm on a dry matter basis of a porphyin compound.

In further preferred embodiments, the lactic acid bacterial cells according to the invention contain at least 0.1 ppm on a dry matter basis of a cytochrome, including at least 0.2 ppm, such as at least 0.5 ppm, including at least 1 ppm, e.g. at least 2 ppm, such as at least 5 ppm, including such as 10 ppm, such as at least 20 ppm, e.g. at least 30 ppm, such as at least 40 ppm, e.g. at least 50 ppm, such as at least 60 ppm, e.g. at least 70 ppm, such as at least 80 ppm, e.g. at least 90 ppm, such as at least 100 ppm on a dry matter basis of a cytochrome.

In accordance with the invention, any lactic acid bacterial starter culture organisms which are of use in the food or feed industry, including the dairy industry, can be used. Thus, the lactic acid bacterial cells can be selected from a lactic acid bacterial species selected from the group consisting of a *Lactococcus* species, a *Streptococcus* species, a *Leuconostoc* species, a *Lactobacillus* species and an *Oenococcus* species.

The lactic acid bacterial cells according to the invention are useful as starter cultures in the production of food and feed products. Accordingly, in a further aspect, the invention relates to a starter culture composition comprising the lactic acid bacterial cell culture according to the invention or the lactic acid bacterial cell according to the invention.

It is convenient to provide the starter culture composition according to the invention as a starter culture concentrate both when used in food and feed production or for the production of metabolites that are generated by the starter culture strains. Typically, such a concentrate contains cells of the starter culture organisms as a non-concentrated fermentate of the respective starter culture strain(s) or in a concentrated form. Accordingly, the starter culture composition of the invention may have a content of viable cells (colony forming units, CFUs) which is at least $10^4$ CFU/g including at least $10^5$ CFU/g, such as at least $10^6$ CFU/g, e.g. at least $10^7$ CFU/g, $10^8$ CFU/g, $10^9$ CFU/g, $10^{10}$ CFU/g, $10^{11}$ CFU/g or $10^{12}$ CFU/g of the composition. Furthermore, the starter culture composition of the invention may have a CFU in the range of $10^4$ to $10^{12}$ CFU/g, $10^5$ to $10^{12}$ CFU/g, $10^6$ to $10^{12}$ CFU/g, $10^7$ to $10^{12}$ CFU/g, $10^8$ to $10^{12}$ CFU/g, $10^9$ to $10^{12}$ CFU/g or $10^{10}$ to $10^{12}$ CFU/g.

The starter culture composition according to the invention can be provided as a liquid, frozen or dried, such as e.g. freeze-dried or spray-dried, starter culture composition.

As it is normal in lactic acid bacterial fermentation processes to apply mixed cultures of lactic acid bacteria, the composition according to the invention comprises in certain embodiments a multiplicity of strains either belonging to the same species or belonging to different species. Accordingly, in a further embodiment, the starter culture composition comprises cells of two or more different lactic acid bacterial strains.

In one embodiment, the composition according to the invention is a composition which further comprises at least one component that enhances the viability of the bacterial cell during storage, including a bacterial nutrient, a vitamin and/or a cryoprotectant. In the case of a composition subjected to a freezing step, a suitable cryoprotectant is selected from the group consisting of glucose, lactose, raffinose, sucrose, trehalose, adonitol, glycerol, mannitol, methanol, polyethylene glycol, propylene glycol, ribitol, alginate, bovine serum albumin, carnitine, citrate, cysteine, dextran, dimethyl sulphoxide, sodium glutamate, glycine betaine, glycogen, hypotaurine, peptone, polyvinyl pyrrolidine and taurine. The cryoprotectant used is advantageously selected from alginate, glycerol, glycine betaine, trehalose and sucrose.

Figure 2:
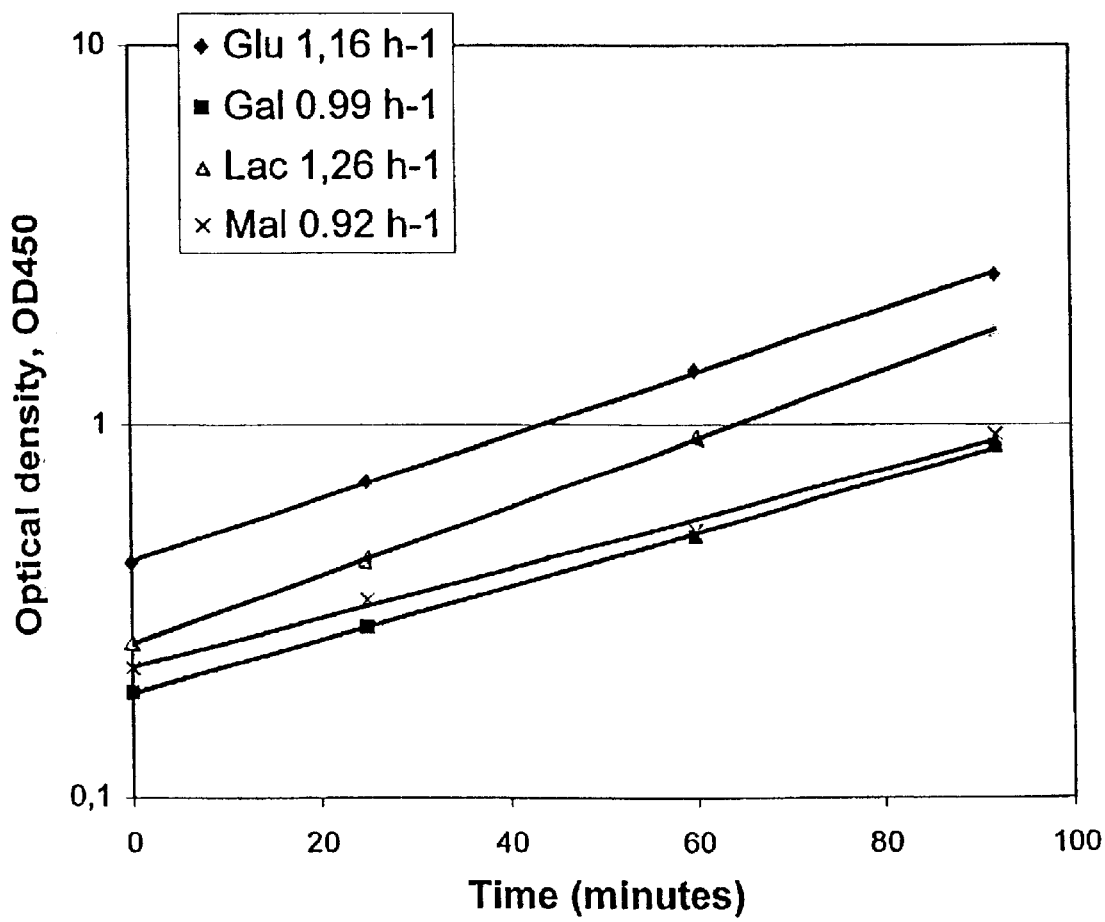

The invention will now be further illustrated in the following non-limiting examples and the figures wherein FIG. 1 shows the growth of *Lactococcus lactis* in a chemostat culture at different dilution rates; and FIG. 2 shows the growth of *Lactococcus lactis* subsp *lactis* FHCY-1 in M17 batch cultures supplemented with four different sugars.

EXAMPLES

Example 1

Activation of ATP synthesis in Lactococcus lactis cultivated in the presence of selected sugars Various strategies can be applied to activate ATP synthesis by the $H^+$-ATPase/ATP synthase complex. One such strategy is to obtain a low ATP/ADP ratio by selecting particular sugar substrates. Some sugars are metabolised readily whereas others are "exotic" to lactic acid bacteria and are for that reason more slowly metabolised. Therefore, by changing the sugar substrate in the growth medium the rate of ATP synthesis can be varied, which can then be exploited to modulate the ATP/ADP ratio in the growing cells.

1.1 Cultivation of *Lactococcus lactis* subsp. *cremoris* in a medium containing glucose as the sole carbon source Wild type *L. lactis* subsp. *cremoris* PJ4662, a derivative of the strain MG1363 containing the pAK80 plasmid (Israelsen et al., 1995) was grown aerobically in defined SA medium (Jensen and Hammer, 1993) supplemented with a growth limiting concentration of glucose (GSA), and in GSA medium further supplemented with haemin (GSA+H), heamin+lipoic acid (GSA+H+L) and lipoic acid alone (GSA+L). The biomass yield was estimated by measuring the optical density at 600nm ($OD_{600}$). The yield of biomass increased by about 12% relative to the yield obtained with GSA when the medium was supplemented with haemin, by about 25% using the haemin+lipoic acid supplement and by about 7% using lipoic acid alone. The results are summarised in Table 1.1 below:

TABLE 1.1

Effect of lipoic acid and haemin on the growth, by-product formation and ATP production of *Lactococcus lactis* subsp. cremoris PJ4662 in SA medium with 0.1% glucose

| | Product formation | | | | | | ATP synthesis | | | |
|---|---|---|---|---|---|---|---|---|---|---|
| Additions to medium | pyruv. mM | lactate mM | acetate mM | acetoin mM | sum mM "pyr"* | Biomass % | Substra televel mM | Total mM | Total Oxphos[a] mM | Oxphos ATP/hex mol/mol |
| glucose | 0.00 | 8.03 | −0.31 | 1.05 | 9.83 | 100.0 | 10.14 | 10.14 | 0.00 | 0.00 |
| glucose, haemin | 0.02 | 6.30 | −0.26 | 2.08 | 10.21 | 111.7 | 10.64 | 11.33 | 0.69 | 0.13 |

TABLE 1.1-continued

Effect of lipoic acid and haemin on the growth, by-product formation and ATP production of *Lactococcus lactis* subsp. cremoris PJ4662 in SA medium with 0.1% glucose

| Additions to medium | Product formation | | | | | | ATP synthesis | | | |
|---|---|---|---|---|---|---|---|---|---|---|
| | pyruv. mM | lactate mM | acetate mM | acetoin mM | sum mM "pyr"* | Biomass % | Substra televel mM | Total mM | Total Oxphos[a] mM | Oxphos ATP/hex mol/mol |
| glucose, haemin lipoic acid | 0.00 | 7.86 | 0.99 | 0.69 | 10.23 | 125.4 | 11.23 | 12.72 | 1.49 | 0.27 |
| glucose, lipoic acid | 0.00 | 8.89 | 0.68 | 0.07 | 9.71 | 106.8 | 10.39 | 10.83 | 0.44 | 0.08 |

[a]oxidative phosphorylation
*total concentration of by-products formed re-calculated into mole of pyruvate. E.g. 1 acteoin molecule = 2 pyruvate molecules The by-products produced by the cultures were estimated by HPLC, and found to depend on the additions to the growth medium. Without any additions the sole by-products formed were lactate and acetoin, with haemin more acetoin was produced and with haemin+lipoic acid also acetate was produced. From the biomass yield and the amounts of by-products produced the total amounts of ATP synthesised and the amount of ATP generated by substrate-level phosphorylation in all 4 experiments can then be calculated (Table 1.1).

Clearly, almost all the ATP that is found in terms of biomass production can be accounted for by substrate phosphorylation. The small excess ATP found in the cultures with haemin or lipoic acid is insignificant. With lipoic acid and haemin added together slightly more ATP (0.27 mol/mol hexose) was found. This amount of ATP could in principle result from oxidative phosphorylation, but could also be the result of less ATP being spent by the $H^+$-ATPase under these conditions.

1.2 Cultivation of *Lactococcus lactis* subsp. cremoris in a medium containing maltose as the sole carbon source

*L. lactis* subsp. cremoris PJ4662 was grown aerobically in defined SA medium (Jensen and Hammer, 1993) supplemented with a growth-limiting concentration of 0.1% maltose (MSA), and in MSA medium further supplemented with haemin (MSA+H), haemin+lipoic acid (MSA+H+L) and lipoic acid alone (MSA+L). The biomass yield was estimated by measuring the optical density at 600nm ($OD_{600}$), see Table 1.2 below. The yield of biomass increased by 33% by haemin addition, 128% by haemin+lipoic acid and 48% by lipoic acid alone.

TABLE 1.2

The effect of lipoic acid and haemin on the growth, by-product formation and ATP production of PJ4662 in SA medium with 0.1% maltose, under conditions of moderate aeration

| Additions to medium | Product formation | | | | | | ATP synthesis | | | |
|---|---|---|---|---|---|---|---|---|---|---|
| | pyruv. mM | lactate mM | acetate mM | acetoin mM | sum mM "pyr"* | Biomass % | Substrat level mM | Total mM | Total Oxphos mM | Oxphos ATP/hex mol/mol |
| maltose | 0.04 | 4.61 | 0.01 | 3.71 | 12.07 | 100 | 12.08 | 12.08 | 0.00 | 0.00 |
| maltose, haemin | 0.17 | 2.56 | −0.16 | 5.28 | 13.30 | 133 | 12.98 | 16.00 | 3.03 | 0.55 |
| maltose, haemin lipoic acid | 0.00 | 2.59 | 6.64 | 1.47 | 12.18 | 229 | 18.82 | 27.62 | 8.81 | 1.59 |
| maltose, lipoic acid | 0.00 | 6.00 | 4.08 | 0.32 | 10.71 | 148 | 14.79 | 17.90 | 3.11 | 0.56 |

*the growth medium was always supplemented with 2 microgram/ml erythromycin
*total concentration of by-products formed re-calculated into mole of pyruvate. E.g. 1 acteoin molecule = 2 pyruvate molecules The by-products produced by the cultures in this experiment were analysed by HPLC and found again to depend on the composition of the growth medium. When maltose was the only addition to the growth medium the products formed were mainly lactate and acetoin, with maltose and haemin added more acetoin was produced and with maltose, haemin and lipoic acid in combination also acetate appeared. With maltose and lipoic acid added mainly lactate and acetate was produced. The total amounts of ATP synthesised and the ATP generated by substrate phosphorylation was calculated in all 4 cases (Table 1.2). When the ATP production from substrate phosphorylation is subtracted from the total ATP yield, it can be seen that a significant amount of ATP is generated by oxidative phosphorylation in the culture supplemented with maltose, haemin and lipoic acid.

It was also tested whether the extent of aeration affected the biomass yield and the amount of ATP produced by oxidative phosphorylation by performing an experiment (Table 1.3) using more vigorous aeration as compared to the experiment illustrated in Table 1.2. This resulted in even further increase in biomass production (+163%) and the ATP produced by oxidative phosphorylation amounted to 2.6 moles of ATP for each mole of maltose consumed.

TABLE 1.3

Effect of lipoic acid and haemin on the growth, by-product formation and ATP production of PJ4662 cultivated under vigorous aeration in SA medium with 0.1% maltose

| | Product formation | | | | | | ATP synthesis | | | |
|---|---|---|---|---|---|---|---|---|---|---|
| Additions to medium | pyruv. mM | lactate mM | acetate mM | acetoin mM | sum mM "pyr"* | Biomass % | Substrate level mM | Total mM | Total Oxphos mM | Oxphos ATP/hex. mol/mol |
| maltose | 0.002 | 4.58 | 0.19 | 3.90 | 12.58 | 100 | 12.8 | 12.8 | 0 | 0 |
| maltose, haemin, lipoic acid | 0.006 | 4.31 | 5.35 | 1.06 | 11.77 | 263 | 17.1 | 33.6 | 16.5 | 2.6 |

*total concentration of by-products formed re-calculated into mole of pyruvate. E.g. 1 acteoin molecule = 2 pyruvate molecules In order to investigate whether or not the surplus of ATP that was found in the cultures cultivated in maltose medium (with haemin and lipoic acid) is due to oxidative phosphorylation it was decided to compare the biomass yield of a wild type strain and a strain which, relative to the wild type strain, has a lower expression of the $H^+$-ATPase complex. For that purpose a mutant strain of the MG1363 strain, PJ4699, was used. In this mutant strain the native promoter of the chromosomal atp operon has been replaced with the nisA promoter (de Ruyter et al., 1996). This mutant only expresses sufficient $H^+$-ATPase for growth in the presence of nisin since the strain was shown to be completely dependent on nisin for growth. This also demonstrates that the $H^+$-ATPase is an essential enzyme for growth of L. lactis (Koebmann et al., 2000).

Surprisingly, in the presence of haemin, this mutant turned out to be capable of growth without nisin. This result demonstrates that haemin actually reconstitutes an active proton pump that can contribute to proton pumping at a reduced activity of the $H^+$-ATPase. This mutant therefore permitted an experiment to be performed where the biomass yield of the wild type strain and the $H^+$-ATPase mutant which had lower expression of the $H^+$-ATPase was compared. If ATP is synthesised by the $H^+$-ATPase complex, then the biomass yield on maltose should be lower in the mutant cells having lower activity of this enzyme, under conditions where oxidative phosphorylation is observed. The growth yield in the mutant strain was indeed decreased by 12% (see Table 1.4) in the strains which have lower expression of $H^+$-ATPase, compared to the wt strain, which demonstrates that the $H^+$-ATPase is partially responsible for the increased biomass yield obtained with slow growing cells in the presence of haemin and lipoic acid and that the basis for this increase is the induction of oxidative phophorylation in the cells.

As a control, also the biomass yield in the absence of haemin/lipoic acid was measured and it was found that the two strains had almost identical yields.

TABLE 1.4

Effect of lipoic acid and haemin on the biomass yield of an atp mutant strain, PJ4699, as compared to a wild type control strain, PJ4662 in SA medium with 0.1% maltose

| Additions to medium | Biomass PJ4662 $OD_{600}$ | Yield PJ4699 $OD_{600}$ |
|---|---|---|
| maltose, haemin, lipoic acid | 0.816 | 0.720 |
| maltose, nisin | 0.304 | 0.300 |

1.3 Cultivation of Lactococcus lactis under conditions of sugar starvation in chemostat cultures Another way of changing the rate of ATP synthesis in lactic acid bacterial cells is to change the concentration of the sugar substrate in the growth medium, i.e. e.g. by cultivating the cells in a chemostat culture at different dilution rates. In such a culture sugar is gradually added to the culture while the cells are growing, which has the effect that the cells are constantly starved for sugar. The growth will be slower than if the sugar concentration was present in excess and the ATP/ADP ratio in the growing cells will be lower as compared to cultivating the cells under conditions without carbon source limitation.

Lactococcus lactis subsp. lactis PJ4662 was grown in Biostat Q fermenter in SA medium supplemented with 0.1% maltose, lipoic acid and haemin. Initially the dilution rate (D) was set at 0.15 $h^{-1}$ and allowed to reach steady state for 48 hours. Then D was changed to 0.25 $h^{-1}$ for 36 hours and finally to 0.4 $h^{-1}$ for 12 hours. Samples were taken from the chemostat culture for the determination of biomass concentration, see FIG. 1. The biomass concentration decreased with increasing dilution rate. A data point (growth rate=0.46) represents an experiment performed in batch culture under otherwise identical growth conditions and is included here for comparison.

Clearly, there is a strong increase in the biomass produced from 0.1% maltose. The biomass increased to $OD_{600}$=1.35 at low D which is 4 times the biomass production observed in a batch culture grown in the absence of haemin and lipoic acid.

In Table 1.5 the ATP production in these cells were calculated. At high dilution rate the number of ATP made through oxidative phosphorylation was comparable (2.19 moles of ATP per mole of hexose) to the values observed in the batch culture (1.59). In contrast, at low dilution rate this value increased dramatically, to 5–6 moles of ATP per mole of hexose.

TABLE 1.5

The effect of sugar starvation in chemostat culture on activation of ATP
production in strain PJ4662 in SA medium with 0.1% maltose, lipoic acid and haemin

| Growth conditions | Product formation | | | | | | ATP synthesis | | | |
|---|---|---|---|---|---|---|---|---|---|---|
| | pyruv. mM | lactate mM | acetate mM | acetoin mM | sum mM "pyr"* | Biomass %** | Substrate level mM | Total mM | Total Oxphos mM | Oxphos ATP/hex mol/mol |
| Chemostat D = 0.15 h$^{-1}$ | 0.043 | 2.99 | 5.14 | 1,33 | 10.83 | 387 | 15.97 | 46.7 | 30.69 | 5.52 |
| Chemostat D = 0.25 h$^{-1}$ | 0.048 | 1.67 | 4.49 | 1.33 | 8.86 | 399 | 13.36 | 48.1 | 34.77 | 6.26 |
| Chemostat D = 0.4 h$^{-1}$ | 0.148 | 0.589 | 9.558 | 0 | 10.30 | 265 | 19.85 | 32.00 | 12.15 | 2.19 |
| Batch culture | 0.00 | 2.59 | 6.64 | 1.47 | 12.17 | 229 | 18.82 | 27.62 | 8.81 | 1.59 |

*total concentration of by-products formed re-calculated into mole of pyruvate. E.g. 1 acteoin molecule = 2 pyruvate molecules
**The biomass is calculated as percentage of a reference culture grown in batch in the absence of hemin and lipoic acid, see Table 1.1
***the growth medium was always supplemented with 2 microgram/ml erythromycin 1.4 Cultivation of *Lactococcus lactis subsp. cremoris* in a medium containing galactose as the sole carbon source Wild type *L. lactis subsp. cremoris* PJ4662, a derivative of the strain MG1 363 containing the pAK80 plasmid (Israelsen et al., 1995) was grown aerobically in defined SA medium (Jensen and Hammer, 1993) supplemented with a growth limiting concentration of galactose and lipoic acid (GaSAL), and in GaSAL medium further supplemented with haemin+lipoic acid (GaSALH). The biomass yield was estimated by measuring the optical density at 600nm ($OD_{600}$). The yield of biomass increased by 30% relative to the yield obtained with GaSAL when the medium was supplemented with haemin (GaSALH). A chemostat experiment was also performed with cells grown on galactose. Here the biomass increased by 75% compared to the biomass obtained in GaSAL medium. The results are summarised in the Table 1.6 below.

TABLE 1.6

Effect of lipoic acid and haemin on the biomass yield of strain PJ4662 in SA medium with 0.1% galactose, lipoic acid and with or without haemin supplement

| Additions to medium | Biomass Yield strain PJ4662 $OD_{600}$ |
|---|---|
| galactose, lipoic acid (Batch culture) | 0.54 |
| galactose, lipoic acid, haemin (Batch culture) | 0.70 |
| galactose, lipoic acid, haemin (chemostat culture, D = 0.15 h$^{-1}$) | 0.94 |

Example 2
Activation of ATP synthesis in *Lactococcus lactis* cultivated under conditions optimised for high biomass production in the presence of either maltose or lactose The experiments presented in Example 1 were all performed in relatively diluted cell cultures and served to demonstrate the principle of activating ATP synthesis in lactic acid bacteria. However, in many cases where lactic acid bacteria are used for industrial purposes the biomass in the fermenters are much more concentrated. To demonstrate that the principle of activation of ATP synthesis also works for such cultures an experiment in media optimised for high biomass production was performed.

2.1 Materials and methods

A commercial mixed strain starter culture of *Lactococcus lactis* was applied in this Example. The cultivations were performed on complex media containing hydrolysed skimmed milk powder, yeast extract, essential vitamins and minerals and either lactose or maltose as carbon source. Furthermore, the media were supplemented with haemin. Medium 1 and Medium 2 were optimised with respect to the cellular yield on respectively lactose and maltose as carbon source. All media were adjusted to an initial pH of 6.5. The cultivations were inoculated with concentrated cell suspensions of the *L. lactis* culture. Air was sparged through the cultivation broths at a rate sufficient to maintain the dissolved oxygen concentration above 50% of saturation level. The cultivations were conducted at a temperature of 30° C. The cultures were allowed to acidify to pH 6.2, and subsequently maintained at pH 6.2 by controlled addition of 13.4 N $NH_4OH$. Samples were collected throughout the cultivations for measurements of the optical density using a Hitachi U-100 Spectrophotometer at 600 OD.

2.2 Results

Table 2.1 shows the final yield of biomass produced under aerobic condition in the presence of haemin and either lactose or maltose. Note that two different experiments are shown for maltose. In the first maltose experiment the same medium (medium 1) as for lactose was used. Here the final yield of biomass was increased by 25% compared to the lactose culture. However, some nutrient(s) are limiting for growth on maltose in this growth medium because higher cell densities are obtained. Therefore, after optimising the growth medium, the yield of biomass on maltose could be further enhanced and reached $OD_{600}$=96 in medium 2, which is two-fold higher than in optimised lactose medium.

TABLE 2.1

Biomass production in pH controlled batch experiments with either lactose or maltose as carbon source and in the presence of haemin.

| Carbon source | Medium | Yield ($OD_{600\ nm}$) |
|---|---|---|
| Lactose | Medium 1. Optimised for growth on lactose. | 48 |
| Maltose | Medium 1 with maltose as carbon source instead of lactose. Not optimised for growth on maltose. | 60 |

TABLE 2.1-continued

Biomass production in pH controlled batch experiments with either lactose or maltose as carbon source and in the presence of haemin.

| Carbon source | Medium | Yield (OD$_{600\,nm}$) |
|---|---|---|
| Maltose | Medium 2. Optimised for growth on maltose. | 96 |

Example 3
Effect of a porphyrin compound on the intracellular ratio [ATP]/[ADP] in *Lactococcus lactis* cultivated in the presence of a slow fermentable carbon/energy source The idea behind the present invention is that growing the cells on a slowly fermented carbon/energy source results in a low cellular energy state (as reflected in the intracellular [ATP]/[ADP] ratio). The low energy state causes subsequently the ATP synthase to work in the ATP synthesis direction resulting in ATP production opposite direction compared to normal and produces ATP which is then reflected in a faster growth and a more efficient conversion of sugar into biomass as presented in the Examples above.

The intracellular concentrations of ATP and ADP was measured to test whether the addition of a porphyrin to a culture growing on a poor carbon/energy source would increase the [ATP]/[ADP] ratio as might be expected if the ATP synthase starts to produce ATP.

3.1 Material and methods

Samples were taken from exponentially growing cultures of *Lactococcus lactis subsp. cremoris* at cell densities between 0.2 and 0.8 (OD$_{600}$). The total intracellular metabolite content were extracted as described previously (Andersen et al., 2001) and the concentrations of ATP and ADP were determined as described in Jensen et al. (1993).

3.3 Results

Table 3.1 shows the ratios of the intracellular concentrations of ATP and ADP in *Lactococcus lactis subsp. cremoris* growing aerobically in defined medium supplemented with lipoic acid and maltose (MSA+L) and in defined medium supplemented with lipoic acid, maltose and haemin (MSA+L+H). The [ATP]/[ADP] ratio was 3.8 in cells grown without hemin and 6.9 in cells grown with haemin, despite the fact that the haemin culture grew at a 30% faster rate and therefore also consume ATP faster. This result demonstrates that more ATP is being generated in the cells growing with haemin compared to the cells without haemin

TABLE 3.1

Effect of haemin on the intracellular [ATP]/[ADP] ratio in cells grown aerobically on defined medium supplemented with maltose

| Additions to medium | Intracellular [ATP]/[ADP] ratio* |
|---|---|
| maltose, lipoic acid | 3.8 (0.6) |
| maltose, lipoic acid, haemin | 6.9 (0.3) |

*Values are average of three determinations with standard deviation given in brackets Example 4
Study of different conditions favouring the increase of yield of ATP and activation of lactose metabolising enzymes.

In the previous Examples an increase yield of ATP was obtained by growing the lactic acid bacteria in the presence of the slowly fermented carbon/energy source maltose. Microorganism will normally adjust the expression of genes according to which enzymes are required under a given set of growth conditions. Thus, in the presence of maltose, the genes involved in maltose uptake and maltose degradation will be expressed whereas the lactose genes will be repressed. And vice versa in the presence of lactose. Therefore, if a culture, which has been growing in the presence of maltose, is suddenly provided with lactose as the carbon/energy source, it will not be able to restart growth immediately. This situation may for instance take place if a starter culture has been cultivated in the presence of maltose and is then inoculated into milk in order to acidify. At the time of inoculation, the culture needs to turn on the lactose specific genes first which then results in a lag-phase for growth and acid production.

In the following it is illustrated how this lag-phase might be eliminated in cultures growing under respiratory conditions.

4.1 Growth under lactose limited conditions

As mentioned above, the objective of the present invention is to reduce the sugar flux through the lactic acid bacterial cell in order to increase the yield of ATP. It was shown in Example 1 that growing the cells on maltose results in a low glycolytic flux even when maltose is present in high concentrations because maltose is less readily metabolised. It was further shown that it is possible to achieve a low glycolytic flux by growing the cells in a fed batch or chemostat set up where lactose is present in such low concentrations that the rate of uptake of lactose into the cells becomes lower than under lactose excess conditions. Under these conditions the yield of ATP will increase similarly as observed in the chemostat experiments in Example 1. Since the cells are now growing in the presence of lactose, the lactose degrading enzymes are already expressed and the cells are ready to start the milk fermentation process without a lag phase.

4.2 Growth on a medium containing galactose as the carbon/energy source

The genes involved in degradation of galactose via the tagatose pathway in lactic acid bacteria are encoded on a plasmid, in an operon where the galactose genes are transcribed from a common promoter together with the genes for lactose uptake and degradation. These genes are all regulated by the lac repressor which binds to the promoter region and prevents transcription in the absence of these sugars. This organisation reflects the fact that lactose is a disaccharide composed of a galactose moiety and a glucose moiety. The actual inducer of the lac operon expression in *Lactococcus* is probably tagatose-6-phosphate which is formed from galactose-6-phosphate (de Vos and Simons, 1994). Therefore, it might be possible to achieve induction of expression of the lactose genes by growing the cells on galactose. Galactose is a slowly fermented carbon/energy source like maltose and results in an increased yield of ATP, see Example 1.

However, the strain used in Example 1 did not have the lactose plasmid which also encodes genes for galactose degradation as described above. Therefore, the growth of the starter culture strain, FHCY-1, was tested on various sugars. FIG. 2 shows the growth curves for this strain in M17 medium supplemented with various sugars as carbon/energy source.

Indeed, the growth on galactose was reduced by approximately 20% compared to lactose, which is similar to growth on maltose. Galactose is therefore a suitable substrate for achieving a low glycolytic flux in lactic acid bacteria and therefore an increased biomass and decreased by-product production.

The expression of the lac operon in the cells grown on the various sugars was also tested by measuring the activity of the enzyme phospho-beta-galactosidase. Samples were taken from the cultures in FIG. 2 and processed as described previously (Jensen and Hammer, 1998). Subsequently, the activity of phospho-beta-galactosidase was determined as the standard determination of beta-galactosidase, except that o-nitrophenyl-beta-D-galactopyranoside 6-phosphate (ONPG-P) was used as the chromogenic substrate instead of o-nitrophenyl-beta-D-galactopyranoside (ONPG).

Table 4.2 shows the result of these measurements. As expected, the activity of phospho$\beta$-D-galactosidase is high in cells FHCY-1 cells grown on lactose and low on glucose and maltose. On galactose, however, the of phospho-$\beta$-D-galactosidase activity was actually increased significantly compared to lactose by 20%. Therefore, starter cultures produced with galactose as the carbon/energy source will contain higher activity of the lactose and galactose degrading enzymes which may also be an advantage in order to obtain acidification immediately after the starter culture is inoculated into for instance a medium containing lactose as the main carbon/energy source.

TABLE 4.2

Expression of phospho-$\beta$-D-galactosidase in FHCY-1 cells growing on various carbon/energy sources

| Carbon/energy source | Specific activity of phospho-$\beta$-D-galactosidase* |
| --- | --- |
| Glucose | 14.8 (4.3) |
| Galactose | 172.2 (12.4) |
| Lactose | 149.5 (1.6) |
| Maltose | 37.5 (8.1) |

*Values are average of two determinations with standard deviation given in brackets 4.3 Use of a mutant with constitutive expression of the lac genes Under conditions where lactose is not present in the growth medium, the lac genes are repressed 10 fold by the lac repressor. A mutant of *Lactococcus lactis* were isolated in which functional lac repressor activity is absent and in which the lac genes are expressed constitutively. Cells of *Lactococcus lactis* subsp. *lactis* strain FHCY-1 were streaked on M17 plates supplemented with x-gal (5-bromo-4-chloro-3-indolyl-$\beta$-D-galctoside) and either lactose or glucose and incubated overnight. The following morning the colonies on the lactose plates had become blue whereas the colonies on the glucose plates were still white or very pale blue. This result shows that x-gal can actually be used as a substrate in these organisms as x-gal apparently is transported by the lactose PTS system and phosphorylated in the process to get x-gal-P which is then hydrolysed by the phospho-beta-galactosidase in these organisms. Strain FHCY-1 was subsequently inoculated into M17 medium supplemented with 0.5% glucose and grown for 3 hours until $OD_{600}$=1. Subsequently, 100 $\mu$l of a $10^4$, $10^5$ and $10^6$ dilution of this culture was plated on M17 medium supplemented with 1% glucose and 100 $\mu$g/ml X-gal and incubated at 30° C. overnight. The following day, the plates were screened for darker blue colonies, and a colony was isolated which had the same colour intensity as colonies from M17x-gal plates supplemented with lactose, which indicated that the lactose genes were turned on in the absence of lactose.

Example 5
Use of mutants impaired in sugar metabolism favouring increased yield of ATP.

Another way of limiting the intracellular sugar flux in a lactic acid bacterial cell is to decrease the activity of some of the enzymes involved in degradation of the sugar in question. For example, either the maltose carrier, maltose phosphorylase or beta-phosphoglucomutase, can be down regulated by replacing the respective native promoter with a weaker promoter, by antisense regulation or by other means of changing the cellular activity of these enzymes. The expression of the maltose specific genes is under the control of maIR and by changing the expression of this regulator it is possible to manipulate the expression of several maltose degrading enzymes simultaneously. Similar strategies can be used to lower the expression of enzymes involved in degradation of other carbon/energy sources in lactic acid bacteria. Galactose is a promising candidate for use in the production of starter cultures. The yield of biomass on galactose can be increased further by decreasing the activity of enzymes involved in galactose degradation or uptake either by screening for mutations with lower uptake of galactose or directly by genetic modification for instance of the activity of the galactose transporter, for instance by replacing the promoter of the transporter gene with a weaker promoter.

Example 6
Use of mutants with enhanced activities of the enzymes involved in oxidative phosphorylation, favouring increased yield of ATP Another means of increasing the yield of ATP is to increase the activity of the components of the respiratory chain, see description above.

6.1 Increased activity and efficiency of the native complement of respiratory components Increased activity of respiratory components can be achieved by increasing the expression of the existing components in the cell, for instance the cytbd system or complex 1. Alternatively, in cells where NADH oxidizing activities (NOX) are active which are uncoupled from proton transport, such activities may be eliminated genetically to increase the efficiency of the respiratory processes.

6.2 Increased activity and efficiency of respiratory chain components from other organisms.

It is also possible to enhance the efficiency of the respiratory system with respect to how many protons are pumped out of the cell for each NADH molecule that is oxidised. For instance some of the components of respiratory chain from *Escherichia coli* and *Bacillus subtilis* are far more efficient in pumping protons out of the cell, see description above, These can be introduced into the lactic acid bacteria by using methods known in the art. In such cases it may be an advantage to eliminate the existing less efficient native respiratory component(s).

6.3 Increased activity and efficiency of the ATP synthase complex

Another way to increase the ATP yield is to increase the activity of the ATP synthase complex, by increasing the expression of the native complex. However, since the STP synthase in lactic acid bacteria normally are engaged in pumping protons out of the cell, this complex may not be optimised for ATP production and it may then be an advantage to introduce into the lactic acid bacteria an ATP synthase from an aerobic organism such as *E. coli, Bacillus subtilis* or another source.

REFERENCES

Andersen, K. B., and von Meyenburg, K. 1980. Are growth rates of *Escherichia coli* in batch cultures limited by respiration?. J. Bacteriol. 144, 114–123.

Andersen, H. V., C. Solem, K. Hammer and Jensen, P. R. 2001. Two fold reduction of phosphofructokinase activity in *L. lactis* results in strong decreases in growth rate and glycolytic flux. *Journal of Bacteriology,* 183, 3458–3467.

Anraku, Y., and Gennis, R. B. 1987. The aerobic respiratory chain of *Escherichia coli*. TIBS 12, 262–266.

Atlas, R. M. 1995. Principles of Microbiology (Mosby-year Book, Inc., Missouri, US), p147.

Brock, M. T., Martinko, J. M., and Parker, J. 2000. Biology of Microorganisms, Ninth edition. Prentice Hall, Upper Saddle River, US.

Bryan-Jones, D. G., and Whittenbury, R. 1969. Haematin-dependent oxidative phosphorylation in *Streptococcus faecalis*. J Gen Microbiol 58, 247–60.

Clarke, D. J., and Knowles, C. J. 1980. The effect of haematin and catalase on *Streptococcus faecalis var. zymogenes* growing on glycerol. J Gen Microbiol 121, 339–47.

de Ruyter, P. G., O. P. Kuipers, and W. M. de Vos, W. M. 1996. Controlled gene expression systems for *Lactococcus lactis* with the food-grade inducer nisin. Appl. Environ. Microbiol. 62:3662–3667.

de Vos, W. M., and Simons, G., 1994. Gene cloning and expression systems in *lactococci*, p.52–105. In M. J. Gasson and W. M. de Vos (eds.), Genetics and biotechnology of lactic acid bacteria. Blackie Academic & Professional, Glasgow, United Kingdom.

Faust and VanDemark, 1970. Phosphorylation coupled to NADH oxidation with fumarate in *Streptococcus faecalis*. Arch Biochem Biophys 137, 392–98

Foster, L. D., and Fillingame, R. H. 1982. Stoichiometry of subunits in the $H^+$-ATPase complex of *Escherichia coli*. J. Biol. Chem. 257, 2009–2015.

Gallin and VanDemark, 1964. Evidence for oxidative phosphorylation in *Streptococcus faecalis*. Biochem Biophys Res Commun 17, 630–35.

Gay, N. J. 1984. Construction and characterisation of an *Escherichia coli* strain with an uncI mutation. J. Bacteriol. 158, 820–825.

Ingledew, W. J., and Poole, R. K. 1984. The respiratory chains of *Escherichia coli*. Microbiol. rev. 48, 222–271.

Ingraham, J. L., Maaløe, O., and Neidhardt, F. C. 1983. Growth of the bacterial cell. (Sunderland, Mass.: Sinauer Associates,lnc.).

Israelsen, H., Madsen, S. M., Vrang, A., Hansen, E. B., and Johansen, E. 1995. Cloning and partial characterization of regulated promoters from *Lactococcus lactis* Tn917-lacZ integrants with the new promoter probe vector, pAK80. Appl. Environ. Microbiol., 61:2540–2547.

Jensen, P. R., Westerhoff, H. V., and Michelsen, O.1993. Excess capacity of $H^+$-ATPase and inverse respiratory control in *Escherichia coli*. EMBO J. 12, 1277–1282.

Jensen, P. R. and Hammer, K. 1993. Minimal requirements for growth of *Lactococcus lactis*. Applied and Evironmental Microbiology. 59, 4363–4366.

Jensen, P. R., and K. Hammer. 1998. The sequence of spacers between the consensus sequences modulates the strength of prokaryotic promoters. Appl. Environ. Microbiol. 64:82–87.

Kashket, E. R. 1985.The proton motive force in bacteria: a critical assessment of methods. Annu. Rev. Microbiol. 39:219–242.

Koebmann, B. J., D. Nilsson, O. C. Kuipers, and P. R. Jensen. 2000. The membrane bound $H^+$-ATPase complex is essential for growth of *Lactococcus lactis*. Journal of Bacteriology, 182, 4738–4743.

Maloney, P. C. 1987. Coupling to an energized membrane: Role of ion-motive gradients in the transduction of metabolic energy. In *Escherichia coli* and *Salmonella typhimurium*, F. C. Neidhardt, ed. (Washington, D.C.20006: American Society for Microbiology), pp. 232–243.

Poole, R. K., and Ingledew, W. J. 1987. Pathways of electrons to oxygen. In *Escherichia coli* and *Salmonella typhimurium*, F. C. Neidhardt, ed. (Washington,D.C.: Am.Soc.Microb.), pp. 170–200.

Pritchard, G. G., and Wimpenny, J. W. 1978. Cytochrome formation, oxygen-induced proton extrusion and respiratory activity in *Streptococcus faecalis var. zymogenes* grown in the presence of haematin. J Gen Microbiol 104, 15–22.

Pugh, S. Y., and Knowles, C. J. 1982. Growth of *Streptococcus faecalis var. zymogenes* on glycerol: the effect of aerobic and anaerobic growth in the presence and absence of haematin on enzyme synthesis. J Gen Microbiol 128, 1009–17.

Ritchey, T. W., and Seeley, H. W. 1974. Cytochromes in *Streptococcus faecalis var. zymogenes* grown in a haematin-containing medium. J Gen Microbiol 85, 220–228.

Ritchey, T. W., and Seely, H. W., Jr. 1976. Distribution of cytochrome-like respiration in *streptococci*. J Gen Microbiol 93, 195–203.

Smalley, Jahrling and VanDemark 1968. Molar growth yields as evidence for oxidative phosphorylation in *Streptococcus faecalis* strain IOCI. J Bac 96, 1595–00.

Sneath, P. H. A., Mair, N. S., Sharpe, M. E., Holt, J. G. 1986. Bergey's Manual of Systematic Bacteriology (Eds. Butler et al.). Volume 2. 1043–1071.

Unden G, Bongaerts J. 1997. Alternative respiratory pathways of *Escherichia coli*: energetics and transcriptional regulation in response to electron acceptors. Biochim Biophys Acta 1320(3):217–34.

von Wachenfeldt C, Hederstedt L. 1992. Molecular biology of *Bacillus subtilis* cytochromes. FEMS Microbiol Lett 79(1–3):91–100.

Whiftenbury, 1964. Hydrogen peroxide formation and catalase activity in the lactic acid bacteria. J Gen Microbiol 35,13–26.

What is claimed is:

1. A method of obtaining an increased yield of biomass of a lactic acid bacterial cell culture, said increased yield is obtained by increasing the yield of ATP in the cells, the method comprising
   (i) providing conditions that result in a reduced glycolytic flux in the cells of the culture, and
   (ii) providing conditions that enable the cells under aerobic conditions to have a respiratory metabolism.

2. A method according to claim 1, wherein the resulting cell biomass is a lactic acid bacterial food or feed starter culture.

3. A method according to claim 1 wherein the increased yield of ATP is obtained by activating the native ATP synthase activity or enhancing the expression of the ATP synthase of the cell.

4. A method according to claim 3 wherein the ATP synthase activity of the cells is activated by increasing the proton gradient of the cells and/or reducing the ATP/ADP ratio.

5. A method according to claim 4 wherein the reduced ATP/ADP ratio is provided by the reduced glycolytic flux in step (i).

6. A method according to claim 1, wherein the reduced glycolytic flux in the cells is provided by cultivating the culture under carbon source limiting conditions.

7. A method according to claim 6 wherein the carbon source limitation is provided by using a growth-limiting concentration of the carbon source.

8. A method according to claim 6, wherein the carbon source limitation is provided by cultivating the cells under fed batch and/or continuous conditions.

9. A method according to claim 6 wherein carbon source limiting conditions are provided by using a carbon source which is not readily metabolised by the cell.

10. A method according to claim 9 wherein the carbon source is selected from the group consisting of ribose, xylose, arabinose, allose, mannose, gulose, idose, galactose, talose and maltose.

11. A method according to claim 6 wherein the carbon source limiting conditions are provided by modifying the cells in order to assimilate the carbon source at a lower rate relative to its parent strain.

12. A method according to claim 3, wherein the increased yield of ATP is provided by increasing the expression of ATP synthase.

13. A method according to claim 12 wherein the expression of ATP synthase is increased by introducing in the cells an increased number of copies of a gene or genes expressing ATP synthase activity.

14. A method according to claim 12 wherein the expression of ATP synthase is increased by inserting a regulatory sequence that enhances expression or by reducing or inhibiting inhibition of the expression of ATP synthase.

15. A method according to claim 3, wherein the ATP synthase activity of the cells is activated by increasing the proton gradient of the cell.

16. A method according to claim 15 wherein the proton gradient is increased by increasing the expression of the native components of the electron transport chain.

17. A method according to claim 15 wherein the proton gradient is increased by increasing expression of NADH dehydrogenase or by reducing or eliminating the expression of a $NAD^+$ regenerating enzyme activity.

18. A method according to claim 17 wherein the $NAD^+$ regenerating enzyme activity is NADH oxidase activity.

19. A method according to claim 15 wherein the proton gradient is increased by increasing the expression of the endogenous cytochromes including cytochrome bd.

20. A method according to claim 15 wherein the proton gradient is increased by introducing a heterologous respiratory chain component.

21. A method according to claim 20 wherein the component is a cytochrome selected from the group consisting of cytochrome type bo, cytochrome type $aa_3$ and cytochrome complex cyt $bc_1$.

22. A method according to claim 1, wherein the conditions that enables the cell under aerobic conditions to have a respiratory metabolism are provided by cultivating the cells in a medium containing a quinone and/or a porphyrin compound or by cultivating the cells under conditions which favour the formation of a quinone, a porphyrin compound and/or a cytochrome.

23. A method according to claim 1, wherein the biomass comprises cells comprising a gene coding for a desired gene product.

24. A method according to claim 23 wherein the expression of the gene is under the control of an inducible or a constitutive promoter.

25. A method according to claim 23 wherein the desired gene product that is encoded is selected from the group consisting of an enzyme and a pharmaceutically active gene product.

26. A method according to claim 25 wherein the enzyme gene product is a milk clotting enzyme.

27. A method according to claim 1, wherein the cell is of a lactic acid bacterial species selected from the group consisting of a *Lactococcus* species, a *Streptococcus* species, a *Leuconostoc* species, a Lactobadilus species and an *Oenococcus* species.

* * * * *